United States Patent
Castignoles et al.

(10) Patent No.: US 11,266,494 B2
(45) Date of Patent: Mar. 8, 2022

(54) ASSEMBLY CONSISTING OF A PAIR OF MULTIFOCAL OCULAR IMPLANTS

(71) Applicant: Cristalens Industrie, Lannion (FR)

(72) Inventors: Fannie Castignoles, Tredrez Locquemeau (FR); Denis Delage, Dinge (FR)

(73) Assignee: Cristalens Industrie

( * ) Notice: Subject to any disclaimer, the term of this patent is extended or adjusted under 35 U.S.C. 154(b) by 0 days.

(21) Appl. No.: 16/650,694

(22) PCT Filed: Oct. 1, 2018

(86) PCT No.: PCT/EP2018/076656
§ 371 (c)(1),
(2) Date: Mar. 25, 2020

(87) PCT Pub. No.: WO2019/068645
PCT Pub. Date: Apr. 11, 2019

(65) Prior Publication Data
US 2020/0281715 A1    Sep. 10, 2020

(30) Foreign Application Priority Data
Oct. 5, 2017  (FR) ........................ 1759329

(51) Int. Cl.
*A61F 2/16*    (2006.01)
(52) U.S. Cl.
CPC .......... *A61F 2/1618* (2013.01); *A61F 2/1621* (2013.01); *A61F 2/1648* (2013.01)
(58) Field of Classification Search
CPC ..... A61F 2/1618; A61F 2/1621; A61F 2/1648
See application file for complete search history.

(56) References Cited

U.S. PATENT DOCUMENTS

| 5,443,507 A | 8/1995 | Jacobi |
| 2013/0033676 A1* | 2/2013 | Zalevsky ........... G02B 27/0037 351/159.02 |
| 2015/0320547 A1 | 11/2015 | Rosen et al. |

FOREIGN PATENT DOCUMENTS

WO    2009027438 A2    3/2009

OTHER PUBLICATIONS

International Search Report for PCT/EP2018/076656, dated Nov. 13, 2018, 4 pages.
(Continued)

*Primary Examiner* — Yashita Sharma
*Assistant Examiner* — Aren Patel
(74) *Attorney, Agent, or Firm* — Lerner, David, Littenberg, Krumholz & Mentlik, LLP

(57) ABSTRACT

An assembly comprising a pair of multifocal ocular implants, wherein each implant has a TFMTF curve, for a pupil of diameter less than or equal to 4 mm, preferably less than 3 mm, having a peak corresponding to the distance vision of the wearer, as well as an asymmetrical peak which spreads between intermediate vision and near vision without discontinuity;
for a first implant, the TFMTF value is greater in intermediate vision than that of near vision;
for the second implant, the TFMTF value is greater in near vision than that of intermediate vision;
the rising edge of the asymmetrical peak of the first implant has, as an absolute value, a mean slope greater than that of its falling edge, whereas the rising edge of the asymmetrical peak of the second implant has, as an absolute value, a mean slope less than that of its falling edge.

6 Claims, 3 Drawing Sheets

(56) References Cited

OTHER PUBLICATIONS

French Search Report for Reference No. 1759329 , dated Oct. 5, 2017, 7 pages.

\* cited by examiner

ASSEMBLY CONSISTING OF A PAIR OF MULTIFOCAL OCULAR IMPLANTS

CROSS-REFERENCE TO RELATED APPLICATIONS

The present application is a national phase entry under 35 U.S.C § 371 of International Application No. PCT/EP2018/076656 filed Oct. 1, 2018, which claims priority from French Application No. 1759329 filed Oct. 5, 2017, all of which are hereby incorporated herein by reference.

FIELD OF THE INVENTION

The present invention relates to an assembly consisting of a pair of multifocal ocular implants.

BACKGROUND OF THE INVENTION

For many years now, people suffering from opacification of the crystalline lens (cataract) have been offered a procedure consisting of the destruction and removal thereof, and its replacement with an intraocular implant.

Thus, it is conventional to position on both eyes of a presbyopic patient (whether he is emmetrope or ametrope) two intraocular implants (implants of the crystalline lens capsule, of the anterior chamber or intracorneal) with multifocal optical surfaces (refractive or preferably diffractive).

The choice of implant can be made according to the living habits of the patient and his requirements. Priority is generally given to distance (far) vision (for example in a situation of driving of a vehicle) and near vision (for example in a situation of reading of a book). But with the ever-increasing use of computers, tablets and smartphones, prioritizing intermediate vision is also an aim (notably illustrated by a situation in which a screen is viewed).

An implant with multifocal optical surfaces (refractive or preferably diffractive) can be characterized by its TFMTF (Modulation Transfer Function Through Focus) curve.

Such a curve represents the quality of the lens (in percentage or in the form of a ratio between 0 and 1of contrast of the image for an initial object having a contrast of 100%) as a function of the distance of vision (which is described in addition in Diopters: 0D=distance vision; +1 to +2D=intermediate vision; 3D=near vision).

Such curves are simulated with an optical simulation software program such as the software program Zemax (trademark) of the company of the same name for intraocular implants placed in a mean eye model.

A TFMTF curve is established for a given spatial frequency. Usually for multifocal implants, the TFMTF at 50 cycles/mm is advantageous. But TFMTF at 25 cycles/mm (coarser objects) and 100 cycles/mm (finer objects) are also advantageous.

A TFMTF curve at 50 cycles/mm (for example) of a given optical profile depends on the pupil of the optical system and the wavelength of the light used.

Thus, preference may be given to a wavelength corresponding to the color green (546 nm), but it can also be advantageous to plot the photopic TFMTF curve corresponding to the integral of the wavelengths of daylight, and also to the scotopic TFMTF curve (night vision).

Similarly, preference is given to a pupil of 3 mm in diameter (corresponding to well-lit vision such as a situation of reading or daytime vision), but the complementarity of TFMTF can be advantageous for pupils of 2 to 6 mm in diameter.

A TFMTF value greater than or equal to 0.15 is considered to provide vision that is nearly satisfactory to the wearer, whereas a TFMTF value greater than or equal to 0.30 is considered to provide distance vision satisfactory to the wearer.

Near vision "VP" is typically +3D (in corneal plane addition) but can be between +2D and +4D.

Intermediate vision "VI" is typically +1.5D (in corneal plane addition) but can be between +1D and +2D.

If the TFMTF curves of an implant placed in an eye make it possible to provide information about the optical quality of the implant, the physical quantity that translates the correct vision of the wearer is its visual acuity.

Visual acuity depends on the TFMTF of the implant, but also other parameters such as the sensitivity to contrast of the wearer. In binocular vision, visual acuity also depends on the neuronal processing of the patient who combines the information coming from his two eyes.

Thus, even if it is not possible to directly simulate the visual acuity (AV) of a wearer as a function of the implant used, it is known that the AV curve has a shape that follows that of the TFMTF curve, but with a wider envelope.

In binocular vision, the superimposition of two peaks present on the TFMTF curves for one and the same addition makes it possible to slightly improve the visual acuity.

Thus, for example, a near visual acuity of 8/10 on one eye and of 8/10 on the other eye can give a binocular visual acuity of 10/10.

This is illustrated in the appended FIG. 1, wherein are shown in solid lines the superimposed TFMTF curves of two identical implants of +3D addition, for a pupil of 3 mm in diameter and a wavelength of 546 nm (on the abscissa: addition expressed in Diopters/on the ordinate: TFMTF at 50 cycles/mm), whereas the estimate of the TFMTF curve in binocular vision is shown in broken lines.

On the other hand, when both eyes have a slightly shifted TFMTF peak (for example with implants of additions of +2.5D and +3D respectively), the binocular AV combines the peaks giving 8/10 at 2.5D and 8/10 at 3D. It is the well-known principle of "Mix and Match" in intraocular implants where two implants identical but with a different addition (same curve shape but shifted near vision peaks) are used.

This is illustrated in the appended FIG. 2 wherein the parameters are the same as those used above with reference to FIG. 1, the characteristic curves of the two implants being referenced A and B.

But the limitation of this practice is that the difference between the two apices of the VI (intermediate vision) and VP (near vision) peaks must be limited to be well-tolerated by the wearer. This difference is usually at 0.5D or even 0.75D (for additions of approximately 2.5D), as the area of overlap between the two curves in near vision is small.

When both eyes have implants with differences in addition greater than 0.75D, there is, among most wearers, a suppressive effect (the "defocused" eye therefore having a very low TFMTF) in VI which will make the VI peak of the adapted eye decrease, and vice versa).

Again, this situation is illustrated in FIG. 3 wherein the parameters are the same as those used above with reference to FIG. 2, the overly large difference between the apices of the peaks being referenced EA.

The present invention aims to palliate these difficulties, by proposing multifocal implants which, when worn together, not only allow the wearer to have good distance vision, but also to enjoy continuous depth of field in binocular vision between intermediate vision and near vision.

SUMMARY OF THE INVENTION

Thus, the present invention relates to an assembly consisting of a pair of multifocal ocular implants, characterized by the fact that:
  each implant of this pair has a TFMTF (Modulation Transfer Function Through Focus) curve, for a pupil of diameter less than or equal to 4 mm, preferably less than or equal to 3 mm, which has a peak corresponding to the distance vision of the wearer, as well as an asymmetrical peak which spreads between intermediate vision and near vision, that is to say without discontinuity between intermediate vision and near vision;
  for a first implant of this pair, the TFMTF value is greater in intermediate vision than that of near vision;
  for the second implant of this pair, the TFMTF value is greater in near vision than that of intermediate vision;
  the rising edge of the asymmetrical peak of the first implant has, as an absolute value, a mean slope greater than that of its falling edge, whereas the rising edge of the asymmetrical peak of the second implant has, as an absolute value, a mean slope less than that of its falling edge.

The expression "mean slope" is understood to mean, in the whole of the present description and the claims, the slope of the imaginary line passing through the highest point and the lowest point of the corresponding edge.

The principle of the present invention is to combine on both eyes of a presbyopic patient (whether he is emmetrope or ametrope) two ocular implants (implants of the crystalline lens capsule, of the anterior chamber or intracorneal) with different multifocal optical surfaces (refractive or preferably diffractive) giving so-called "complementary" TFMTF curves.

Owing to the present invention, the wearer of such implants is given a continuous depth of field in binocular vision between intermediate vision and near vision, which translates into a visual acuity greater than 5/10 over this whole region.

According to other non-limiting and advantageous features of the invention:
  the overlap of said asymmetrical peaks corresponds to a TFMTF value of at least 0.10;
  the overlap of said asymmetrical peaks corresponds to a TFMTF value of at least 0.15;
  the apex of each asymmetrical peak has a TFMTF value at least equal to 0.15;
  the respective TFMTF values at the apices of the peaks corresponding to distance vision have a difference of less than 30%.

BRIEF DESCRIPTION OF THE DRAWINGS

Other features and advantages of the invention will become apparent on reading the following description of a preferred embodiment of the invention. This description is given with reference to the appended drawings wherein.

DETAILED DESCRIPTION OF THE INVENTION

As has been specified above, the present invention results from the fact that the advantage of having the combination of two so-called "complementary" TFMTF is to make it possible to better merge the vision of both eyes of the wearer of the implants, while permitting a greater difference between the two apices of the VI (intermediate vision) and VP (near vision) peaks than with the prior devices mentioned above which apply the "Mix and Match" principle.

Figure 1:
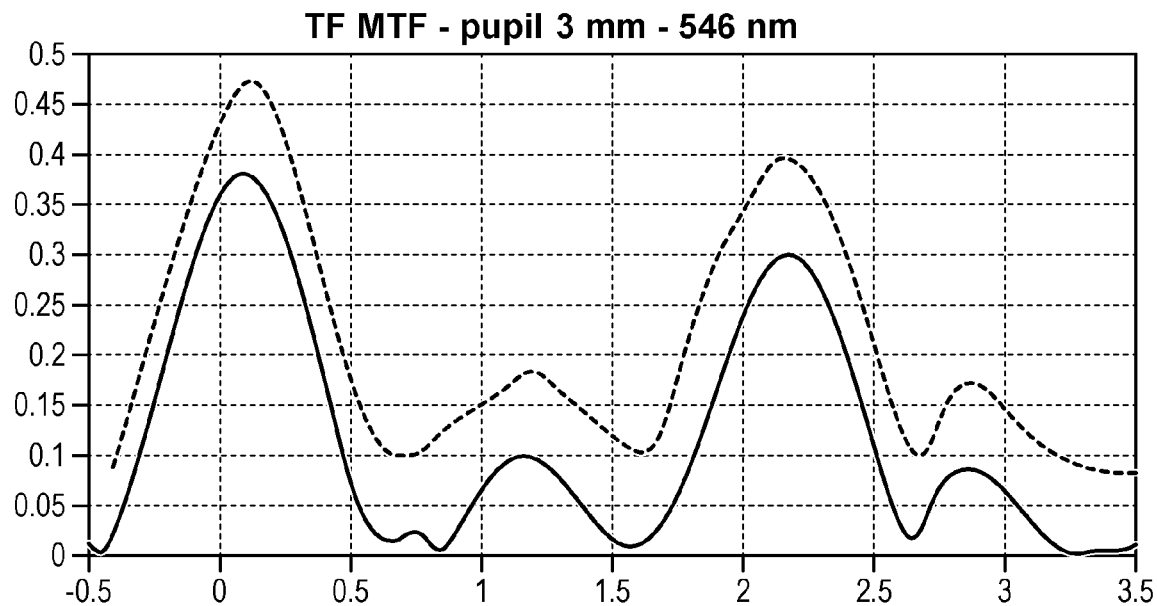
FIGS. 1 to 3, as specified above, illustrate the state of the art in the field of the invention.
Figure 2:
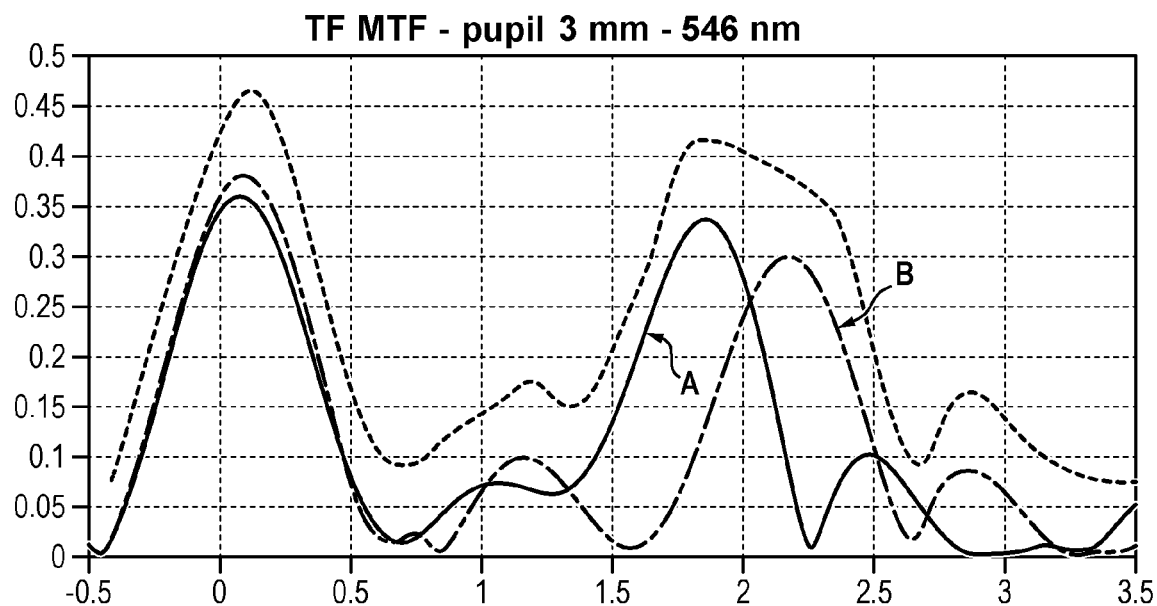
Figure 3:
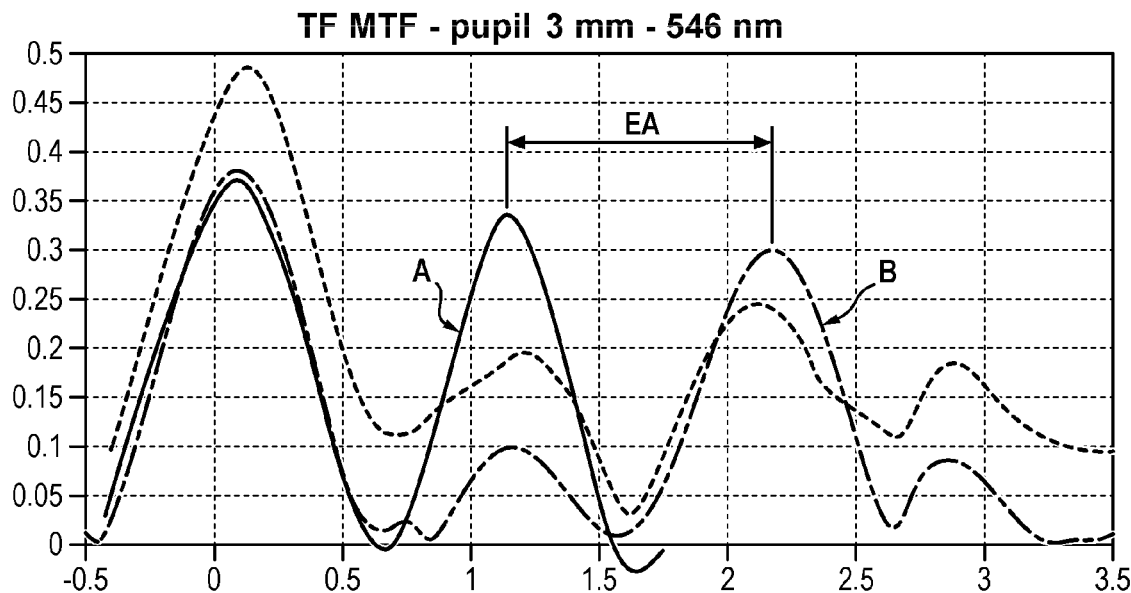
Figure 4:
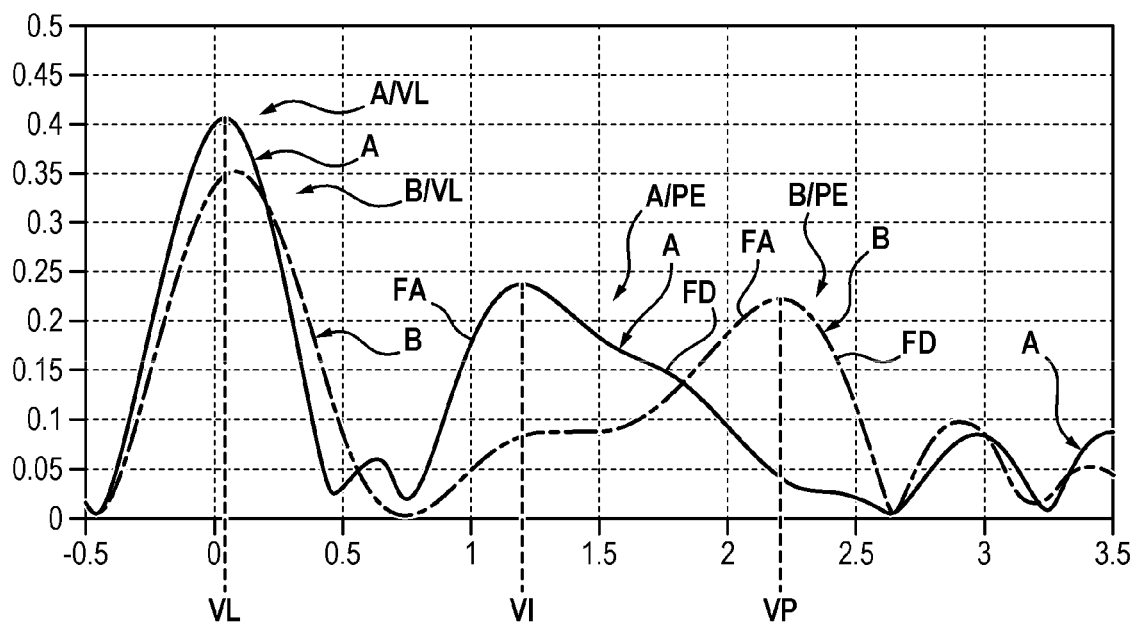
FIG. 4 is a representation, on one and the same diagram of the TFMTF curves of two implants forming an assembly according to the invention, for a pupil of 3 mm in diameter and a wavelength of 546 nm (on the abscissa: addition expressed in Diopters/on the ordinate: TFMTF at 50 cycles/mm)
Figure 5:
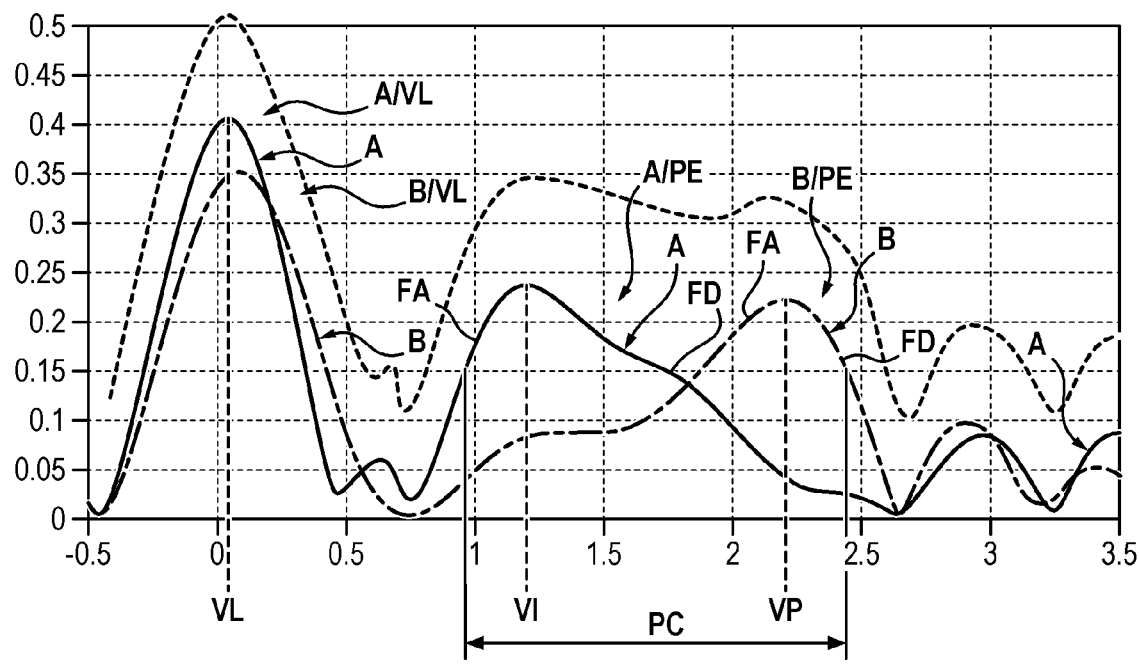
FIG. 5 is an identical view to the preceding one to which is also added the estimate of the TFMTF in binocular vision.

The reader is referred to the appended FIGS. 4 and 5 for a description of the preferred TFMTF curves of the two implants forming the assembly according to the invention.

In these figures, the respective TFMTF curves of each of the two implants are referenced A and B and correspond for example to the dominant eye and the non-dominant eye of the wearer respectively (or conversely).

It should first of all be noted that each A and B curve has a peak, A/VL and B/VL respectively, corresponding to the distance vision of the wearer (with correction of the refractive errors if necessary.)

These peaks are similar for both implants. Under all circumstances, the respective TFMTF values at the apices of the peaks A/VL and B/VL have a difference of less than 20% and preferably less than 10%.

Moreover, the two curves A and B have an "asymmetrical widened peak", A/PE and B/PE respectively (with respect to a conventional multifocal) which spreads between intermediate vision VI and near vision VP. In other words, there is no distinction of two distinct peaks, but on the contrary, there is continuity of the TFMTF between VI and VP while preserving a minimum level of 0.10, preferably 0.15.

In addition, for a first implant of the assembly corresponding to curve A, the TFMTF value is greater in intermediate vision VI than that of near vision VP.

And conversely, for the second implant of the assembly corresponding to curve B, the TFMTF value is greater in near vision VP than that of intermediate vision VI.

Finally, the two curves complement one another in such a way that they have an asymmetrical profile with an "overall slope" that is gentler in their area of overlap.

In other words, the rising edge FA of the asymmetrical peak A/PE of the first implant has, as an absolute value, a mean slope greater than that of its falling edge FD, whereas the rising edge FA of the asymmetrical peak B/PE of the second implant has, as an absolute value, a mean slope less than that of its falling edge FD.

Advantageously, the TFMTF two curves A and B overlap at a threshold greater than or equal to 0.15.

Thus, in binocular vision, the wearer of the pair of implants of the assembly according to the invention has a TFMTF greater than 0.15 over a much more extended range of distance or depth of field (EDOF), typically of 1D to 2.5D (which corresponds to a distance of vision of 40 cm to 1 m).

Comparatively, "Mix and Match" (M&M) systems of the state of the art offer a clear vision of 40 cm to 66 cm—or even 75 cm—in M&M+2.5D/+3D and M&M+2.25D/+3D respectively.

Figure 6:
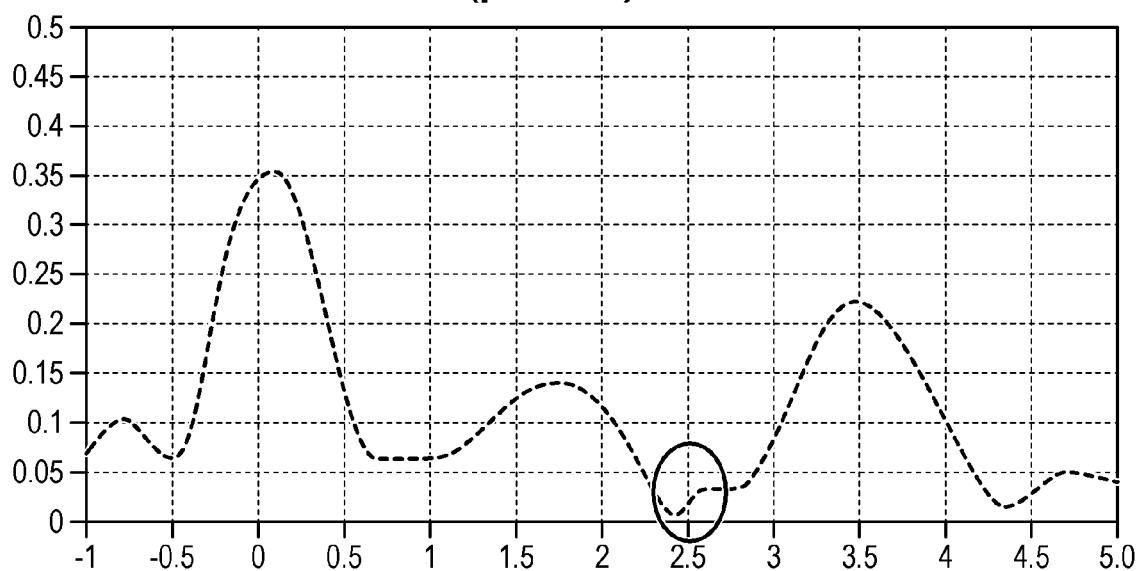
FIG. 6 is a TFMTF curve in binocular vision of implants of the prior art.

In addition, the combination of two so-called "complementary" TFMTF also provides a more advantageous binocular vision than that of a trifocal implant having a peak of distance vision VL, a peak of intermediate vision VI, and a peak of near vision VP, with cancellations of the TFMTF between each of these peaks, which translates into an absence of continuous vision between near vision VP and intermediate vision VI. This is illustrated in FIG. 6 where the area of cancellation of the TFMTF is marked by a circle.

The depth of field PC of the binocular TFMTF allows a continuity between its near and intermediate vision without any drop in sharpness between the two, as appears on the curve in broken lines in FIG. 5.

In a well-known manner, one of the main drawbacks associated with multifocal implants is the presence of halos.

Thus, with a bifocal implant, in night vision, and mainly when driving (that is to say when the "useful" vision is distance vision), the wearer can be bothered by the halo created by the near vision VP peak.

On the other hand, with a trifocal implant, the distance vision is associated with two halos corresponding to the near vision and intermediate vision peaks. However, since the height of these two peaks is smaller, the effect of these halos is less bothersome for the wearer than with a conventional bifocal implant.

In other words, the wearer better tolerates several weaker halos rather than a strong and well-defined halo.

Thus, the use of two "complementary" implants according to the invention makes it possible to create a continuous or diffuse halo which is less bothersome in conditions of distance vision and especially of night driving.

Those skilled in the art will proceed with the fabrication of two intraocular implants (implants of the crystalline lens capsule, of the anterior chamber or intracorneal) with different multifocal optical surfaces (refractive or preferably diffractive), so that these have the features expressed above.

As for implants of the prior art, these implants can be put in place on the eyes of a patient using an injector. And when this placement is performed in the crystalline lens capsule, they are introduced in the folded position through a slit of small dimensions provided for this purpose.

Although the present description has been made in relation to intraocular implants, the present invention also applies to intracorneal implants and to "piggybacks", i.e. implants placed in front of the crystalline lens capsule.

The invention claimed is:

1. An assembly comprising a pair of multifocal ocular implants intended to be worn at the same time by the same person, wherein:
    each implant of this pair of multifocal ocular implants has a TFMTF (Modulation Transfer Function Through Focus) curve, for a pupil of diameter less than or equal to 4 mm and at a wavelength of 546 nm, which has a peak corresponding to distance vision, and an asymmetrical peak, which spreads between intermediate vision and near vision, without discontinuity between intermediate vision and near vision;
    for a first implant of this pair of multifocal ocular implants, the TFMTF value of said TFMTF curve is greater in intermediate vision than the TFMTF value of near vision;
    for a second implant of this pair of multifocal ocular implants, the TFMTF value of said TFMTF curve is greater in near vision than the TFMTF value that of intermediate vision;
    the rising edge of the asymmetrical peak of the first implant has, as an absolute value, a mean slope greater than that of the falling edge of said asymmetrical peak,
    whereas the rising edge of the asymmetrical peak of the second implant has, as an absolute value, a mean slope less than that of the falling edge of said asymmetrical peak.

2. The assembly according to claim 1, wherein the overlap of said asymmetrical peaks corresponds to a TFMTF value of at least 0.10.

3. The assembly according to claim 2, wherein the overlap of said asymmetrical peaks corresponds to a TFMTF value of at least 0.15.

4. The assembly according to claim 3, wherein the apex of each asymmetrical peak has a TFMTF value at least equal to 0.15.

5. The assembly according to claim 1, wherein the respective TFMTF values at the apices of the peaks corresponding to distance vision have a difference of less than 30%.

6. An assembly according to claim 1, wherein the TFMTF curve is considered for a pupil of diameter less than or equal to 3 mm.

* * * * *